US008271089B2

(12) United States Patent
Dinsmoor et al.

(10) Patent No.: US 8,271,089 B2
(45) Date of Patent: Sep. 18, 2012

(54) HYBRID RECTIFICATION FOR RECHARGING AN IMPLANTABLE MEDICAL DEVICE

(75) Inventors: David A. Dinsmoor, St. Paul, MN (US); Todd A. Kallmyer, Tempe, AZ (US); Joel A. Anderson, Brooklyn Park, MN (US); Timothy J. Denison, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 669 days.

(21) Appl. No.: 12/418,291

(22) Filed: Apr. 3, 2009

(65) Prior Publication Data
US 2010/0256710 A1 Oct. 7, 2010

(51) Int. Cl.
*A61N 1/378* (2006.01)
(52) U.S. Cl. ............................... 607/33; 607/34; 607/61
(58) Field of Classification Search .............. 607/33–34, 607/61
See application file for complete search history.

(56) References Cited

U.S. PATENT DOCUMENTS

| 5,633,577 | A | | 5/1997 | Matsumae et al. | |
|---|---|---|---|---|---|
| 5,702,430 | A | * | 12/1997 | Larson et al. | 607/61 |
| 5,702,431 | A | * | 12/1997 | Wang et al. | 607/61 |
| 5,733,313 | A | * | 3/1998 | Barreras et al. | 607/33 |
| 6,553,263 | B1 | * | 4/2003 | Meadows et al. | 607/61 |
| 6,764,446 | B2 | * | 7/2004 | Wolinsky et al. | 600/300 |
| 6,879,809 | B1 | | 4/2005 | Vega et al. | |
| 7,184,836 | B1 | * | 2/2007 | Meadows et al. | 607/33 |
| 7,279,843 | B2 | | 10/2007 | Baarman et al. | |
| 7,295,878 | B1 | | 11/2007 | Meadows et al. | |
| 7,444,184 | B2 | | 10/2008 | Boveja et al. | |
| 2005/0107841 | A1 | | 5/2005 | Meadows et al. | |
| 2005/0131495 | A1 | * | 6/2005 | Parramon et al. | 607/61 |
| 2006/0129205 | A1 | | 6/2006 | Boveja et al. | |
| 2009/0323381 | A1 | * | 12/2009 | Wuidart | 363/126 |

FOREIGN PATENT DOCUMENTS
EP 0987814 A1 3/2000

OTHER PUBLICATIONS
PCT International Search Repot and Written Opinion dated May 25, 2010.
* cited by examiner

*Primary Examiner* — Joseph Stoklosa
(74) *Attorney, Agent, or Firm* — Beth L. McMahon

(57) ABSTRACT

A charging system is disclosed. In one embodiment, the system includes a charging unit having a primary coil, and an implantable medical device comprising a secondary coil to receive charge from the primary coil. The implantable medical device further includes a half-wave voltage-doubling rectifier coupled to the secondary coil, a full-wave rectifier coupled to the secondary coil, and a rechargeable power source. Control logic is provided to periodically configure the rechargeable power source to receive charge from a selected one of the voltage-doubling circuit and the full-wave rectifier in a manner that increases rate at which charge is transferred from the secondary coil to the rechargeable power source. The control logic may configure the rechargeable power source to receive charge based on one or more monitored conditions which may include, for example, an indication of a current, a voltage, a coupling coefficient, back-scatter, and temperature.

30 Claims, 10 Drawing Sheets

HYBRID RECTIFICATION FOR RECHARGING AN IMPLANTABLE MEDICAL DEVICE

FIELD OF THE INVENTION

This invention relates to Implantable Medical Devices (IMDs) and, in particular, to energy transfer devices, systems and methods for IMDs.

BACKGROUND OF THE INVENTION

IMDs for producing a therapeutic result in a patient are well known. Examples of such IMDs include, but are not limited to, implantable drug infusion pumps, implantable neurostimulators, cardioverters, cardiac pacemakers, defibrillators and cochlear implants. Such IMDs may treat a variety of symptoms or conditions including, but not limited to, chronic pain, migraine headaches, tremor, Parkinson's disease, epilepsy, incontinence, gastroparesis, heart failure, tachycardia, and bradycardia.

A common element in all of these IMDs is the need for electrical power in the device. The IMD requires electrical power to perform its function, which may include driving an electrical infusion pump, providing an electrical neurostimulation pulse, recording signals and/or providing an electrical cardiac stimulation pulse, for example.

Typically, a power source for an IMD can take one of two forms. The first form utilizes an external power source that transcutaneously delivers energy via wires or radio frequency energy. Having electrical wires which perforate the skin is disadvantageous due, in part, to the risk of infection. Further, continuously coupling patients to an external power source for therapy is a large inconvenience.

A second type of power source utilizes primary cell batteries as the energy source of the IMD. This can be effective for low-power applications, such as cardiac pacing devices. However, such primary cell batteries usually do not supply the lasting power required to perform more energy-intensive functions. In some cases, such as involving an implantable artificial heart, a primary cell battery might last the patient only a few hours. In less extreme cases, a primary cell unit might expel its energy in less than a year. This is not desirable due to the need to explant and re-implant the IMD or a portion of the device.

One way to address the aforementioned limitations involves transcutaneously transferring electrical power through the use of inductive coupling. Such electrical power may then be optionally stored in a rechargeable (secondary) battery or capacitive element. Such a rechargeable battery may be used for directly powering the IMD. When the battery has mostly or totally expended its capacity, the battery may be recharged. This is accomplished transcutaneously using electromagnetic coupling from an external power source that is temporarily positioned on the surface of the skin. Most often this will involve inductive coupling, but could include other types of electromagnetic coupling such as RF coupling.

Transcutaneous energy transfer through the use of electromagnetic coupling generally involves the placement of two coils positioned in close proximity to each other on opposite sides of the cutaneous boundary. An internal, or "secondary" coil may be part of or otherwise electrically associated with the IMD. An external, or "primary" coil is associated with the external power source or recharging device. According to one method, the recharging device drives the primary coil with an alternating current. This induces a current in the secondary coil through inductive coupling. This current may then be used to power the IMD and/or to recharge an internal power source. Alternatively, RF coupling between the primary and secondary coils may be utilized for this purpose.

For IMDs, the efficiency at which energy is transcutaneously transferred is crucial for several reasons. First, the inductive coupling has a tendency to heat surrounding components and tissue. The amount of heating of surrounding tissue, if excessive, can be deleterious. By increasing the efficiency of the energy transfer between the primary and secondary coils, heating of the tissue is minimized. Moreover, the time required to complete the recharge session is minimized, thereby maximizing patient convenience. Additionally, by allowing the transfer of more energy during a shorter period of time, IMDs may be employed that have higher power requirements and that provide greater therapeutic and other advantages to the patient. Therefore, techniques for maximizing the efficiency at which energy is transcutaneously transferred are needed.

SUMMARY OF THE INVENTION

The current disclosure provides techniques and mechanisms for recharging a rechargeable power source. This rechargeable power source may be a battery or capacitive element within an implantable medical device. Energy may be transferred from a primary coil of an external recharging device to a secondary coil of the implantable medical device to thereby recharge the rechargeable power source. A charging module within the implantable medical device may be used to control how this recharge occurs.

According to one aspect, the charging module of the implantable medical device may utilize either a full-wave rectifier or a half-wave voltage-doubling (HWVD) rectifier to supply current to the rechargeable power source. For instance, in some circumstances, such as at times of poor coupling between the primary and secondary coils, more efficient recharge will be achieved if the HWVD rectifier is used for this purpose. In other cases, such as during times of relatively good coupling between the primary and secondary coils, more efficient recharge is achieved by using the full-wave rectification.

According to one aspect, control logic is provided to determine which one of the HWVD and full-wave rectification will be used at a given instant in time to provide current to the rechargeable power source. This determination may be made, for instance, based on one or more conditions that are monitored within the system. Such conditions may include current flow within one or more nodes of the system, voltage levels at one or more nodes, temperature at one or more nodes, and/or a measure of the back-scatter generated by the secondary coil.

The process of monitoring a condition and re-configuring the charging module based on the measured value for the condition may be repeated at periodic intervals. The length of these intervals varies between thirty seconds and two minutes in one embodiment. In another embodiment, these intervals may be even shorter, with re-configuration occurring every ten seconds. This periodic reconfiguring of the system will ensure that if the patient alters the relative position of the primary and secondary recharge coils during a recharge session, thereby modifying the coupling efficiency between these coils, the configuration will be adjusted as needed to take the alternation into account.

In another embodiment, the control logic operates in an open-loop mode. According to this aspect, the control logic configures the full-wave rectifier to provide current to the power source for a first predetermined period of time. Thereafter, control logic re-configures the system to allow the HWVD rectifier to provide current to the power source for a second period of time that may be the same as, or different from, the first time period. This process may then be repeated so that current is alternately provided by full-wave rectification and HWVD rectification.

In one embodiment, a recharge system is disclosed. This recharge system includes a charging power source, a rechargeable power source, and a half-wave voltage-doubling (HWVD) rectifier coupled to receive energy from the charging power source to recharge the rechargeable power source. The system further includes a full-wave rectifier coupled to receive energy from the charging power source to recharge the rechargeable power source. Control logic is provided to increase a rate at which the rechargeable power source is recharged by controlling which one of the HWVD rectifier and the full-wave rectifier is recharging the rechargeable power source at any given time.

Another aspect of the disclosure relates to a system that includes a recharging device having a primary coil. The system further includes an implantable medical device comprising a secondary coil to receive energy from the primary coil, a HWVD rectifier coupled to the secondary coil, a full-wave rectifier coupled to the secondary coil and a rechargeable power source. Control logic is provided to periodically re-select to which one of the HWVD rectifier and the full-wave rectifier the rechargeable power source is coupled during recharge, thereby increasing efficiency of recharging the rechargeable power source.

A method of recharging a rechargeable power source of an implantable medical device is likewise disclosed. The method includes coupling a primary recharge coil to a secondary recharge coil of the implantable medical device. The method further includes sensing a condition associated with the coupling between the coils and coupling the rechargeable power source to receive charge from the secondary recharge coil via one of full-wave rectification or HWVD rectification based on the sensed condition.

A storage medium is further disclosed that stores programmed instructions. These instructions control recharge of a rechargeable power source within an implantable medical device according to a method that includes determining which one of full-wave rectification and HWVD rectification will result in a higher flow of charge to the rechargeable power source, and coupling the rechargeable power source to receive charge via the one of full-wave rectification and HWVD rectification that will result in a higher flow of charge.

Other aspects of the invention will become apparent to those skilled in the art from the following description and the accompanying drawings.

DETAILED DESCRIPTION OF THE INVENTION

Figure 1:
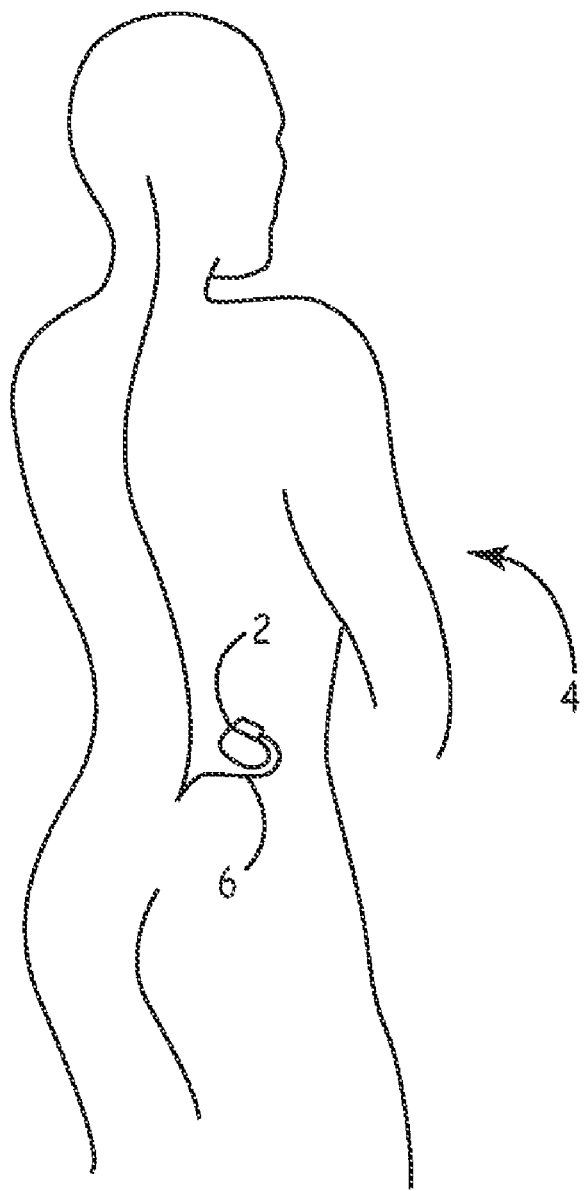
FIG. 1 is a diagram of an Implantable Medical Device implanted in a patient.

The current disclosure provides mechanisms and techniques for optimizing the amount of energy that is harvested during a recharge session by an Implantable Medical Device (IMD) that includes a rechargeable power source. During recharge, a primary coil of an external recharging unit may be positioned close to, or in contact with, the skin of the patient in the vicinity of the IMD. Inductive or radio frequency (RF) energy may be transferred by the primary coil and received by a secondary coil that is located within, or that is otherwise associated with, the IMD. The received energy may then be used to replenish the rechargeable energy source (e.g., rechargeable battery) that is powering the IMD.

The efficiency with which the secondary coil may receive and harvest the energy may depend on various factors associated with the implant scenario. For instance, based on the body type of the patient and/or the type of therapy that is being delivered by the IMD, the IMD may be implanted relatively close to the patient's skin. In other cases, the IMD may be implanted more deeply within the patient's body. For instance, the IMD may be located at a depth of more than three centimeters from the skin in what is considered a "deep-implant scenario".

As the implant depth increases, the recharge efficiency will typically decrease. For instance, in an inductive recharge system, the degree of flux shared between the primary and secondary coils decreases by the cube of the separation distance, leading to a sharp decline in the amount of energy that may be harvested per unit time. Thus, as distance between primary and secondary coils increases, a longer period of time will be required to completely replenish the rechargeable power source.

Another factor that may affect recharge efficiency relates to orientation of the secondary recharge coil within the patient's body. In some implant scenarios, the primary plane of the secondary recharge coil that is associated with the IMD may be relatively parallel to the surface of the patient's skin. In other scenarios, the secondary recharge coil may be rotated somewhat relative to the surface of the skin. The angle of this rotation may be difficult to determine, and may change over time based on a patient's posture and/or the surgical approach that was used during implant. In general, as this angle of rotation increases, the efficiency with which the secondary coil can harvest the recharge energy will decrease.

Still other factors may affect the efficiency of a given recharge session. For instance, the ability of the patient to effectively locate a primary recharge head over the IMD will affect how efficiently recharge will be completed.

For at least the foregoing reasons, there is some variability associated with the recharge coupling efficiency that may be achieved between an external recharging device and the secondary coil carried by an IMD. Moreover, the coupling efficiency may change during the course of a recharge session if the patient moves the primary coil, shifts body position, and so on.

The current disclosure provides techniques and mechanisms for maximizing recharge efficiency regardless of the implant scenario and patient compliance considerations. In accordance with these techniques, a system is provided to receive current from the secondary coil during a recharge session. During some situations, the system is configured to operate as a half-wave voltage-doubling (HWVD) rectifier that results in voltage doubling across the secondary coil. In other situations, the circuit is configured to operate as a full-wave (FW) rectifier. In one embodiment, control logic monitors system conditions to determine when re-configuration of the system will occur. This results in a system that provides an increased amount of energy to a rechargeable power source for a given recharge time, thereby lengthening operating time of the IMD and increasing the time required between recharge sessions. In another embodiment wherein the power received is being used directly to power the IMD, this system makes more power available for use by the IMD.

FIG. 1 is a system diagram of one type of system that may usefully employ the concepts disclosed herein. In this system, an exemplary IMD 2 is implanted in patient 4. IMD 2 may be any number of medical devices such as an implantable therapeutic substance delivery device, an implantable drug pump, a cardiac pacemaker, a cardioverter or defibrillator, a device to deliver electrical stimulation pulses for a neurological or muscular condition, a device to deliver electrical stimulation to alleviate pain, or any other IMD for delivering therapy. This therapy may be delivered via one or more therapy connections 6, which may be one or more leads and/or catheters.

Figure 2:
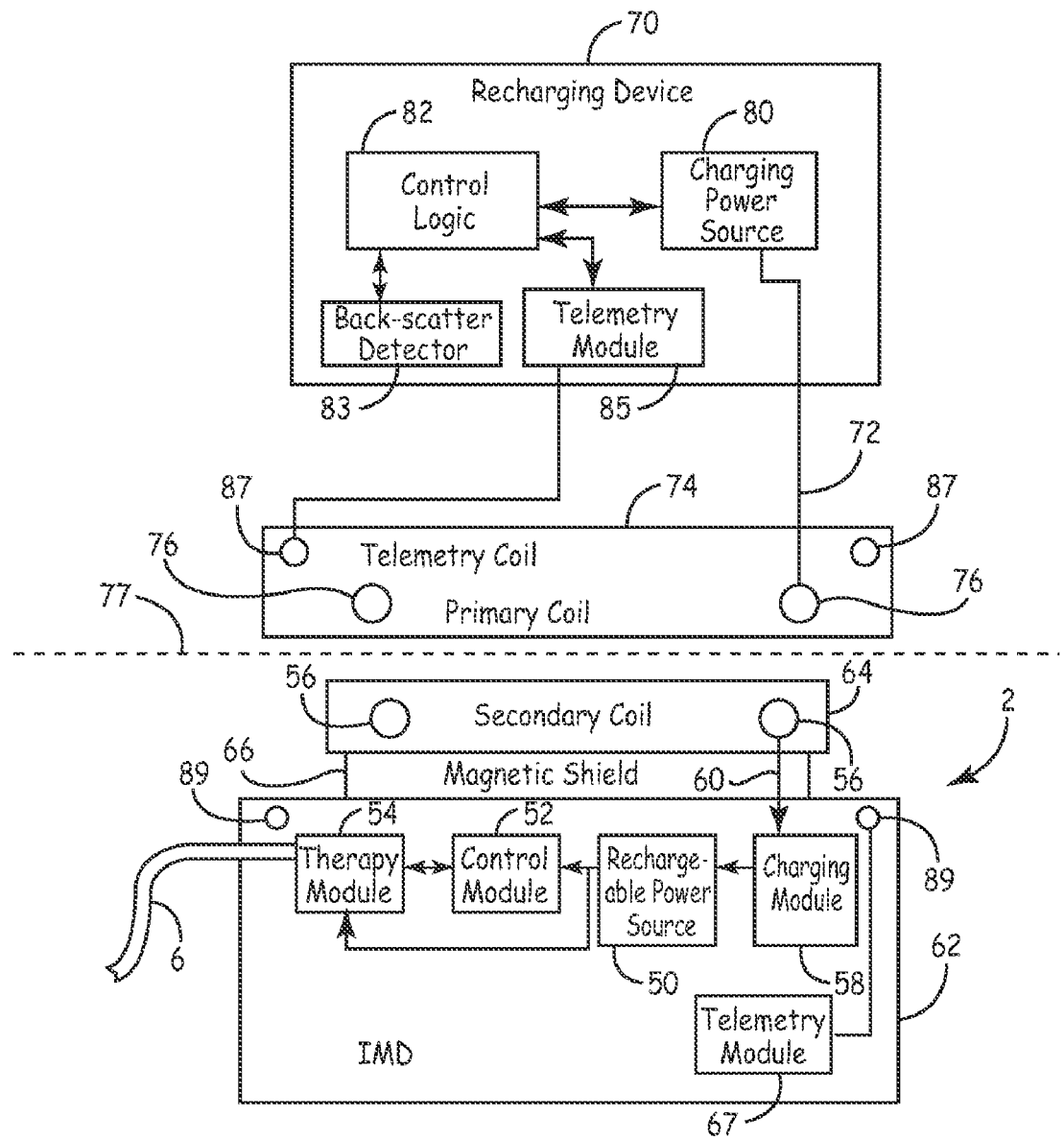
FIG. 2 is a block diagram of one embodiment of an Implantable Medical Device that may usefully employ techniques according to the current disclosure.

FIG. 2 is a block diagram of one embodiment of IMD 2. According to the current invention, IMD 2 includes a rechargeable power source 50. Rechargeable power source 50 may be any of a variety of rechargeable power sources including a chemically-based battery or a capacitor or super-capacitor. In one embodiment, rechargeable power source 50 is a lithium ion battery. Any other type of rechargeable battery suitable for powering an IMD may be used according to the current invention.

Rechargeable power source 50 is coupled to a control module 52, which includes circuitry to control therapy delivered to the patient. Control module 52 may include one or more microprocessors, application-specific integrated circuits (ASICs), digital signal processors (DSPs), field-programmable gate arrays (FPGAs), discrete electronic components, control logics, sensors, and/or other circuitry.

Control module 52 is further coupled, and provides power to therapy module 54. Therapy module 54 delivers some form of therapy to patient 4. This therapy may include controlled delivery of a substance and/or electrical stimulation. For example, in one embodiment, therapy module 54 may include one or more output pulse generators such as capacitive elements, voltage regulators, current sources, and/or switches that are coupled to rechargeable power source 50 directly or through control logic 52. Therapy module 54 may deliver electrical pulses to patient 4 via a combination of electrodes. Therapy module 54 is coupled to patient 4 through one or more therapy connections 6 such as leads and/or catheters.

In one embodiment, rechargeable power source 50 is coupled to a secondary coil 56 (shown in cross-section) through a charging module 58. During a recharge session, a current is induced in secondary coil 56 in a manner to be discussed below. This current is provided via connection 60 to charging module 58, which controls the charging of rechargeable power source 50. The manner in which this is performed is described below.

Rechargeable power source 50, charging module 58, control logic 52, and therapy module 54 are generally contained in a hermetically sealed housing 62. Secondary coil 56 may be attached to, or positioned on, an exterior surface of sealed housing 62 through connection 60. For instance, secondary coil 56 may be contained within a second housing 64 that is positioned adjacent to sealed housing 62. In an alternative embodiment, secondary coil 56 may be contained in housing 62 along with the other electronics.

In one embodiment, a magnetic shield 66 may be positioned between secondary coil 56 and housing 62. The primary purpose of magnetic shield 66 is to substantially increase the amount of energy captured by the secondary coil. Magnetic shield 66 also protects rechargeable power source 50, control logic 52, therapy module 54 and charging module 58 from electromagnetic energy when secondary coil 56 is utilized to charge rechargeable power source 50.

FIG. 2 further illustrates an external recharging device 70 which may be used to recharge rechargeable power source 50. External recharging device 70 is coupled via cable 72 to an antenna 74 (shown in cross-section). In an alternative embodiment, recharging device 70 and antenna 74 may be combined into a single housing. In yet another implementation of recharging device 70, a single coil may serve as both primary recharge coil 76 and telemetry coil 87. In this case, control logic 82 selects which one of telemetry module 85 and charging power source 80 drives the coil at a given time.

Antenna 74 includes a primary coil 76 shown in cross-section. During a recharge session, primary coil 76 is positioned proximate to secondary coil 56 on an opposite side of cutaneous boundary 77 (shown dashed). Recharging device 70 generates a current in primary coil 76. When primary coil 76 is positioned proximate to secondary coil 56, the current in primary coil 76 electromagnetically couples this primary coil to secondary coil 56. In one embodiment, this electromagnetic coupling is inductive coupling, although other forms of coupling (e.g., RF coupling) are possible. The electromagnetic coupling results in a current being generated in secondary coil 56. This current is provided to charging module 58, which controls a rate at which rechargeable power source 50 is recharged.

Recharging device 70 drives primary recharge coil 76 via charging power source 80. Charging power source 80 may itself be rechargeable. For instance, charging power source 80 may include rechargeable batteries to allow a patient who is engaged in a recharge session to be somewhat ambulatory during this process. In this embodiment, a desktop recharging device (not shown) which is coupled to an AC or DC power source (e.g., via a wall outlet) may be used to periodically recharge charging power source 80 when recharging device 70 is not in use. In another embodiment, recharging device 70 may be coupled directly to a source of AC power, such as a standard wall outlet during the recharge session.

Charging device 70 may further include control logic 82. Control logic 82 initiates and controls recharging sessions with IMD 2. Control logic 82 may include one or more microprocessors, FPGAs, ASICs, DSPs, microsequencers, discrete components, and/or other electronic circuit components. Control logic 82 may be coupled to a back-scatter detector 83 which is capable of detecting energy that is back-scattered from secondary coil 64. In one embodiment, this is used to determine a coupling coefficient that is, in turn, used to determine the coupling efficiency achieved between primary coil 74 and secondary coil 56. This is described further below.

Recharging device 70 may further include a telemetry module 85 that is coupled to a telemetry coil 87. The telemetry module 85 may be used to transmit telemetry downlink transmissions to the IMD 2. These communications are received by telemetry coil 89 of IMD 2 and processed by telemetry module 67 of IMD 2 so that programmed instructions, commands, and/or other data may be received by the IMD. Additionally, telemetry module 67 and telemetry coil 89 of IMD 2 may be used to transmit data and other information to telemetry module 85 of recharging device 70 during telemetry uplink transmission.

It will be appreciated that recharging device 70 and IMD 2 are merely exemplary. Many alternative configurations are possible for both of these devices. Various logical functions may be partitioned differently. For instance, control logic 52 and therapy module 54 of IMD 2 may be combined into a single logic block, and so on. Thus, the implementations shown in FIG. 2 are to be considered illustrative in nature only.

In FIG. 2, secondary coil 56 is shown proximate to cutaneous boundary 77, with the plane in which this coil lies being approximately parallel to cutaneous boundary 77. This allows a magnetic field generated by a current within primary coil 76 to readily couple with secondary coil 56. Efficient inductive coupling may be harder to achieve when secondary coil 56 is farther away from cutaneous boundary 77 (e.g., more than 3 centimeters away) and/or if the plane in which secondary coil 56 lies is not parallel to cutaneous boundary 77. This results in less efficient energy transfer between primary coil 76 and secondary coil 56. When this occurs, recharge efficiency can never-the-less be increased via the various techniques described herein.

As discussed above, to harvest the energy provided by primary coil 76 to secondary coil 56, some type of rectification may be performed. This may be accomplished in several ways.

Figure 3A:
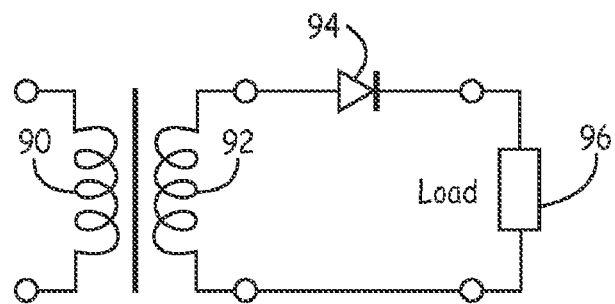
FIG. 3A is a circuit diagram of a half-wave rectifier.

FIG. 3A is a circuit diagram of a half-wave rectifier. During a recharge session, a primary coil 90 of a type that may be driven by a recharging unit is coupled to secondary coil 92 of an IMD via inductive or RF coupling. During a positive-going portion of the waveform, diode 94 is forward biased. As a result, energy flows into load 96, which may be a rechargeable power source. However, during a negative-going portion of the received waveform, diode 94 is not conducting current, and the energy transferred by primary coil 90 is essentially discarded.

Figure 3B:
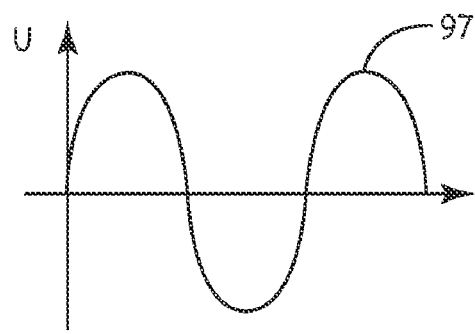
FIGS. 3B and 3C are waveform diagrams illustrating input and output waveforms, respectively, associated with half-wave rectification.
Figure 3C:
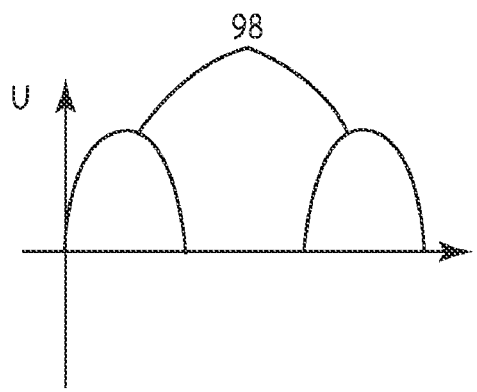

FIGS. 3B and 3C illustrate the input and output waveforms associated with half-wave rectification. In particular, FIG. 3B illustrates an AC waveform that is transferred by primary coil 90 to secondary coil 92. FIG. 3C illustrates the energy transfer (e.g., the current flow) to load 96. This diagram illustrates the manner in which roughly half of the energy is discarded by the half-wave rectification.

In contrast to half-wave rectification, full-wave rectification transfers energy during both the negative- and positive-going portions of the input waveform. This is shown in reference to FIGS. 4A-4C.

Figure 4A:
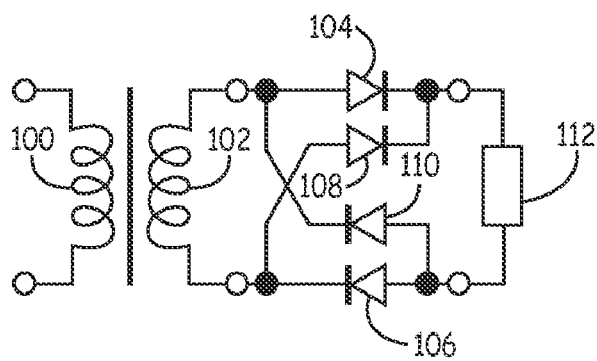
FIG. 4A is a circuit diagram of a full-wave rectifier.

FIG. 4A is a circuit diagram of a full-wave rectifier. During a recharge session, primary coil 100 is coupled to secondary coil 102 via inductive or RF coupling. During a positive-going portion of the waveform, diodes 104 and 106 are forward biased while diodes 108 and 110 are reversed biased. Current flows through the forward-biased diodes to load 112, which may be a rechargeable power source. Conversely, during a negative-going portion of the input waveform, diodes 104 and 106 are reverse biased while diodes 108 and 110 are forward biased. Again, current flows through the forward-biased diodes to load 112.

Figure 4B:
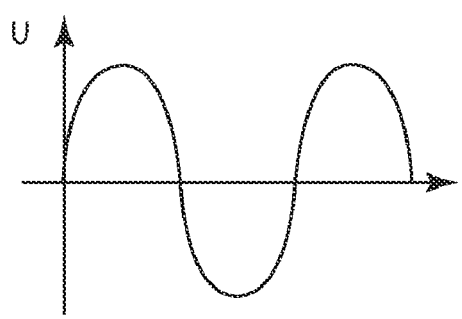
FIGS. 4B and 4C are waveform diagrams illustrating input and output waveforms, respectively, associated with full-wave rectification.
Figure 4C:
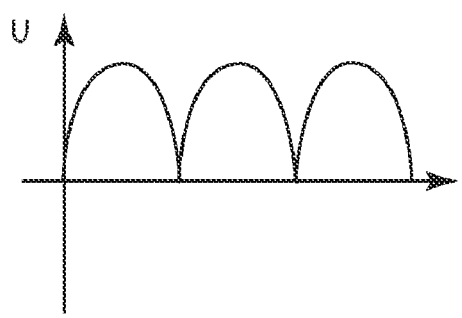

FIG. 4B is an input waveform of the type shown in FIG. 3B. When this input waveform is coupling primary coil 100 to secondary coil 102, an output waveform associated with full-wave rectification is generated to load 112. This output waveform is illustrated in FIG. 4C. As shown in FIG. 4C, both the negative-going and positive-going portions of the input waveform of FIG. 4B result in energy being transferred to load 112. Thus, energy is not discarded as occurs during half-wave rectification. This benefit is obtained at the expense of a full-wave rectification circuit having more components than the half-wave rectification circuit, as may be appreciated by comparing the circuits of FIGS. 4A and 3A.

Figure 5A:
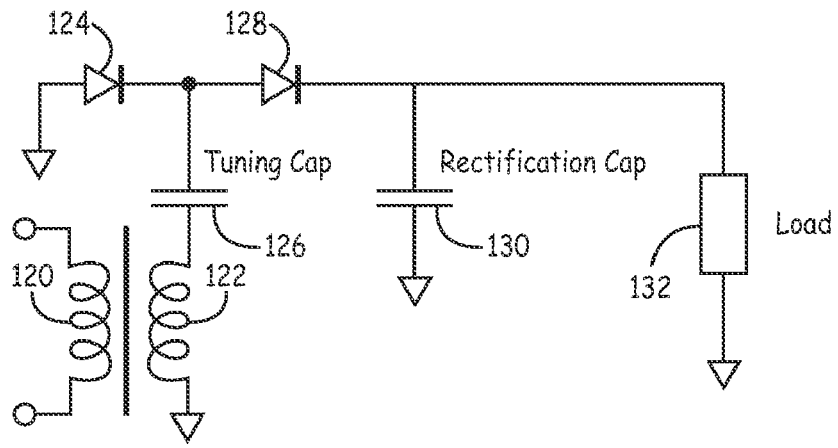
FIG. 5A is a circuit diagram of a half-wave voltage-doubling rectifier according to one aspect of the current disclosure.

FIG. 5A is a circuit diagram according to one aspect of the current invention. During a recharge session, primary coil 120 is coupled to secondary coil 122 via an inductive or an RF link to thereby transfer energy to an IMD. There are two phases of operation for this circuit, the "pumping" phase and the "recharging" phase, as follows.

During the pumping phase, the voltage on secondary coil 122 is falling and current is being sunk through coil 122. As this occurs, current flows through diode 124 and "pumps" tuning capacitor 126. As a result, the top plate of capacitor 126 is held within a voltage diode drop (for diode 124) of ground. The bottom plate of capacitor 126 goes to a negative voltage. At this time, no current flows through diode 128.

During the recharging phase, the voltage on secondary coil 122 is rising and current is sourced through the secondary coil 122. This current flows through diode 128 to rectification capacitor 130. The voltage on the top plate of the tuning capacitor 126 is clamped to a diode drop (for diode 128) above the voltage on the top plate of rectification capacitor 130. In this phase, the voltage on tuning capacitor 126 builds on the voltage generated during the pumping phase. Since the voltage swings across the inductor are symmetric, a voltage-doubling effect occurs during the recharging phase because of the pumping action during the pumping phase. This voltage-doubling effect does not occur if only a single diode half-bridge (FIG. 3A) or full-bridge rectifier (FIG. 4A) is used. The generated voltage is available to provide a charge to load 132, which may be a rechargeable power source.

The half-wave voltage-doubling (HWVD) rectification of FIG. 5A is of benefit when the coupling between primary coil 120 and secondary coil 122 is poor. This may be appreciated by returning to the full-wave rectification circuit of FIG. 4A. Assume for this example that load 112 is a rechargeable battery that has a voltage of 2.5V. Therefore, when current flows to the rechargeable battery via either diode 104 or diode 108, voltage at the input of the conducting diodes will be clamped to the battery voltage of 2.5 volts plus the approximately 0.7 volt diode drop across the conducting diode, or about 3.2 volts. If coupling between primary coil 100 and secondary coil 102 is poor such that the induced voltage across secondary coil is something less than 3.2 volts, current will not flow through either diode 104 or diode 108 and no current will flow to the battery. A similar situation exists with the half-wave rectification circuit of FIG. 3A.

Next, consider the same rechargeable battery of the foregoing example coupled across rectification capacitor 130 as load 132 of FIG. 5A. When two volts is induced across secondary coil 122, the voltage-doubling effect of the circuit of FIG. 5A allows four volts to be provided at the input of diode 128. This is above the minimum 3.2 volts needed to allow current to flow to the battery. Thus, recharge is allowed to continue until the voltage across secondary coil 122 drops to around 1.6 volts, or about half of the 3.2 volts needed to allow current to flow to the battery.

Figure 5B:
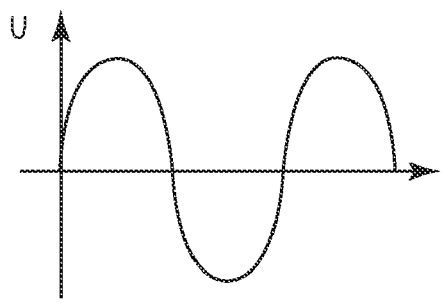
FIGS. 5B and 5C are waveform diagrams illustrating input and output waveforms, respectively, associated with half-wave voltage-doubling rectification.

FIG. 5B is an input waveform of the type shown in FIGS. 3B and 4B. When this input waveform is coupling primary coil 120 to secondary coil 122, an output waveform is generated that results in a voltage-doubling effect described above.

Figure 5C:
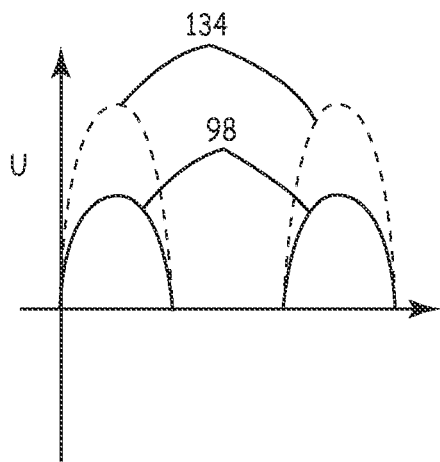

FIG. 5C illustrates the output waveform generated by the circuit of FIG. 5A. The voltage levels represented by output waveform 134 (shown dashed) are provided at the input to diode 128. Output waveform 134 is shown in contrast to the output waveform 98 (FIG. 3C) generated by the circuit of FIG. 3A. As may be appreciated, the peak voltage amplitude of waveform 134 is approximately twice the amplitude of the voltage waveform 98 generated by the circuit of FIG. 3A. This voltage amplitude is also about twice the amplitude of the voltage that would be generated by the full-wave rectification of FIG. 4C under comparable coupling scenarios (e.g., the same coupling efficiency), thereby illustrating the voltage-doubling capabilities of the circuit of FIG. 5A.

The voltage-doubling effects of the circuit of FIG. 5A allow recharge to occur when coupling efficiency is poor, as previously described. This may occur, for instance, when the primary and secondary coils are not fully aligned and/or are separated by a distance. As coupling efficiency improves, a point will be reached at which use of full-wave rectification will result in better current flow to the load than that provided by the circuit of FIG. 5A. This is described in reference to FIG. 6.

Figure 6:
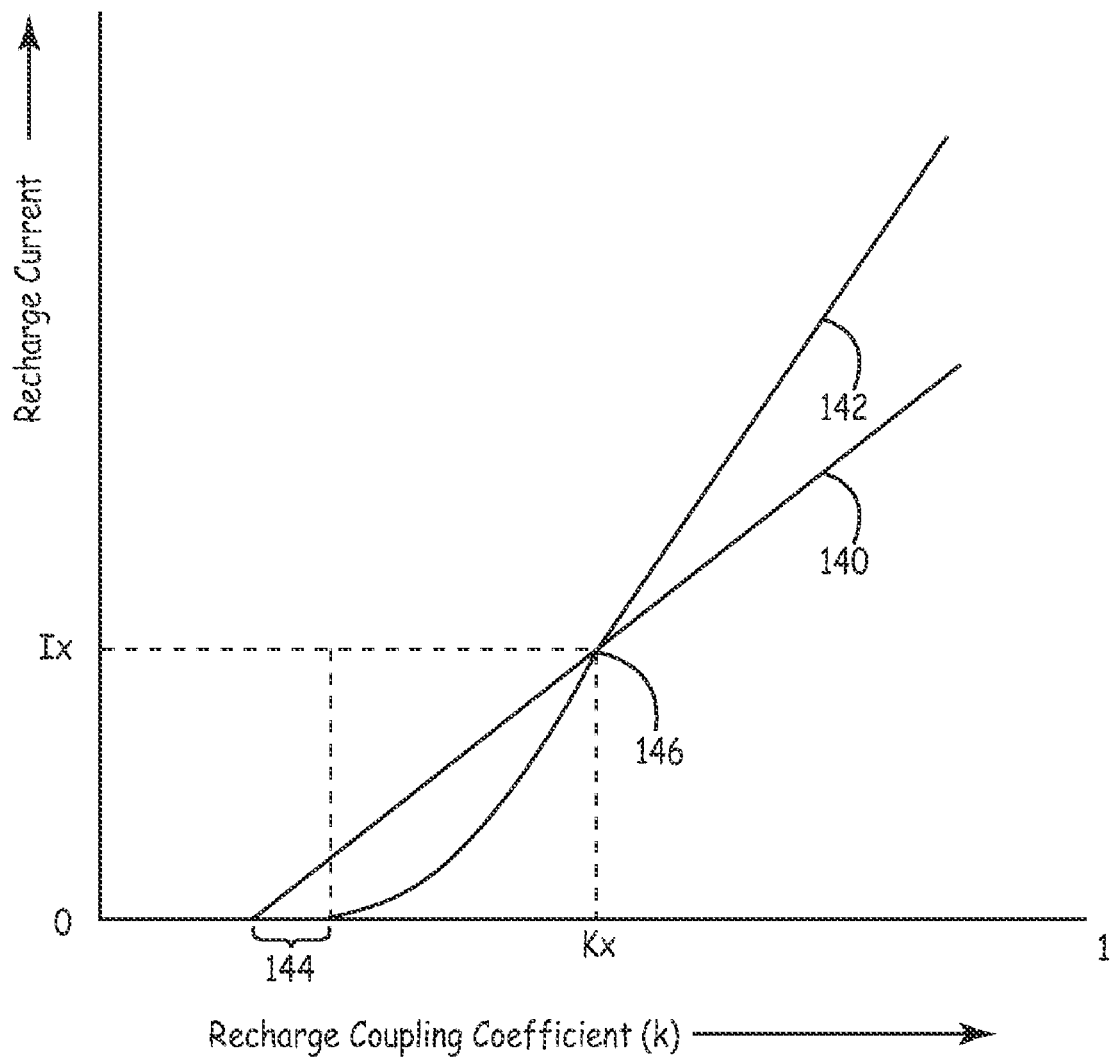
FIG. 6 is a conceptual waveform diagram illustrating coupling efficiency versus recharge current for several types of rectification circuits.

FIG. 6 is a conceptual waveform diagram illustrating coupling efficiency versus recharge current for several circuit configurations. The x-axis of the diagram corresponds to the values for a coupling coefficient k, values of which range from 0 to 1. When the coupling efficiency is 0, no flux is coupling the primary coil to the secondary coil. Conversely, as the coupling efficiency approaches 1, almost all flux will couple the primary coil to the secondary coil. It should be noted that in practice, obtaining perfect coupling is not achievable, as there is always some flux generated by the primary coil which will not couple with the secondary coil.

The y-axis of the diagram of FIG. 6 corresponds to recharge current that is flowing to load such as a rechargeable battery. The amplitude of the current generated to the load will depend on aspects of the circuit configuration, such as the size of the primary coil and secondary coil apertures, the number of turns in each coil, the material construction of the two coils, and so on. Therefore, the diagram of FIG. 6 does not include specific units of measure for current. Rather this diagram is intended to convey trend data that will generally correspond to any type of coil configuration.

According to the trend data of FIG. 6, waveform 140 represents current generated by a HWVD rectifier of the type shown in FIG. 5A as the coupling coefficient k varies from 0 to a value approaching 1. In contrast, waveform 142 represents recharge current generated by a full-wave rectifier of the type shown in FIG. 4A as the coupling coefficient k varies in the same manner.

Several observations may be made by comparing waveforms 140 and 142. First, for lower coupling coefficient values, a range of such values will always exist at which recharge current provided by a full wave rectification circuit will drop to zero while that provided by the HWVD rectifier is still non-zero. This is shown as range 144 in FIG. 6. As discussed above, this range is made possible by the voltage-doubling effects of a circuit such as shown in FIG. 5A, which extends the range at which recharge may continue to occur. This "coupling extension" phenomenon will exist regardless of the specific type of coil configuration used by the HWVD rectifier.

Another observation involves the slopes of the two waveforms 140 and 142. The waveform 142 associated with full-wave rectification has a steeper slope than waveform 140 associated with the HWVD circuit. A cross-over point 146 exists at the intersection of the two waveforms. The coupling coefficient at the cross-over point is shown as $k_x$ and the recharge current that exists at this time, which may be referred to as the "cross-over current", has an amplitude of $I_x$.

The coupling efficiency is lower than $k_x$ when coupling is relatively poor, as when the primary and secondary coils are misaligned or are separated by some distance, as in a deep-implant scenario involving a coil separation of larger than 3 cm. In this situation, the voltage-doubling effects of the HWVD rectifier such as are shown in FIG. 5C will supply a larger current to a load such as a rechargeable power source. However, for a coupling coefficient value that exceeding $k_x$, the full-wave rectification circuit of FIG. 4A will provide a larger current to the load because full-wave rectification utilizes both the positive- and negative-going phases of the waveform induced within the secondary coil, rather than effectively discarding the negative-going phase of the waveform. While the cross-over point, as well as the value for $k_x$, will vary based on the configuration of the primary and secondary coils in the manner discussed above, such a cross-over point will always exist.

According to the current disclosure, the characteristics associated with the circuits of FIGS. 4A and 5A may be employed to obtain a charging module that will maximize recharge efficiency regardless of the coupling coefficient k. This is discussed in reference to FIG. 7.

Figure 7:
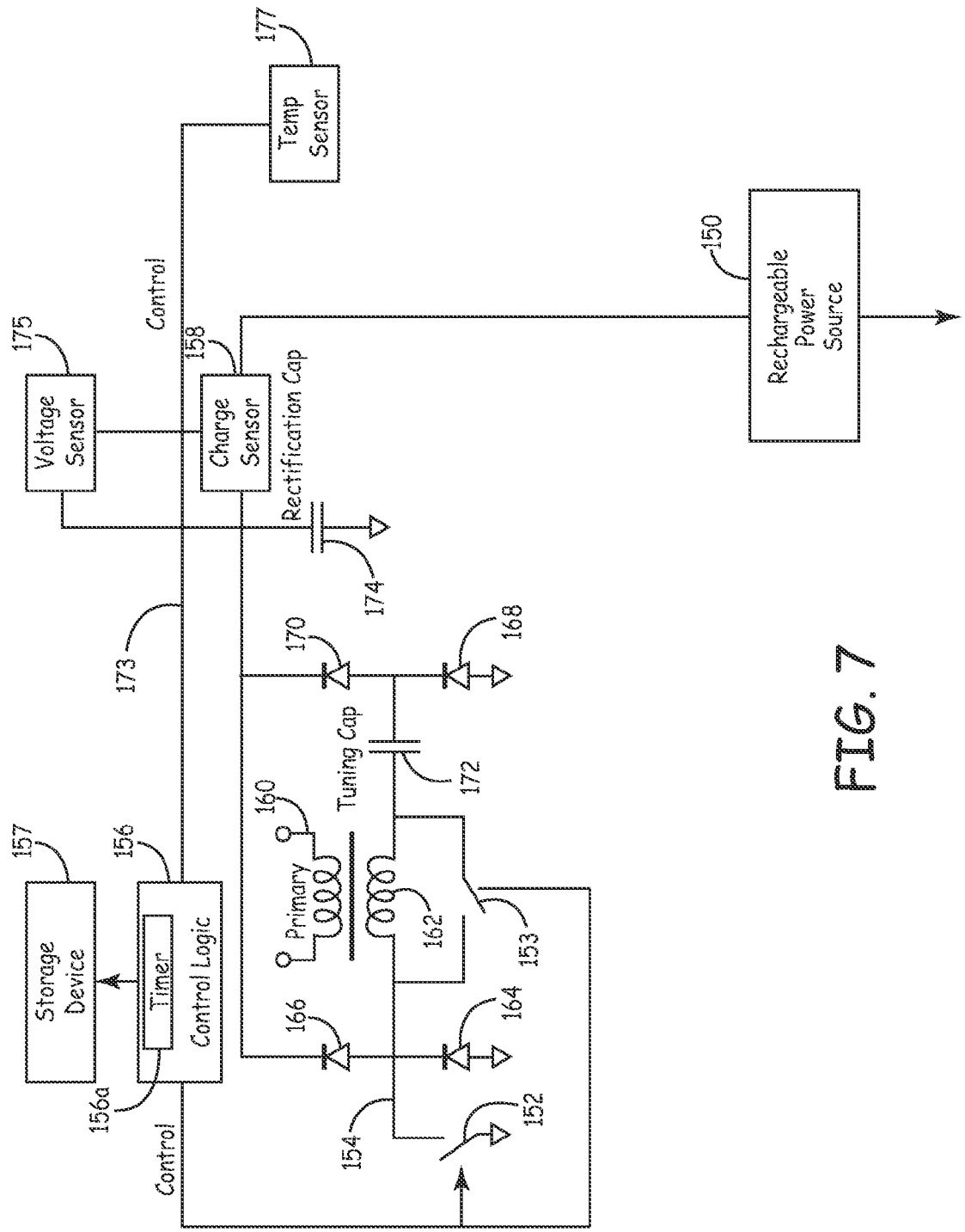
FIG. 7 is a circuit diagram according to one embodiment of the disclosure.

FIG. 7 is a system diagram according to one embodiment of the disclosure. The circuit shown coupled to secondary coil 162 may be included within a charging module used to recharge a rechargeable power source of an IMD. For instance, this circuit may be contained within charging module 58 of FIG. 2. Alternatively, this circuit may be included in another type and/or configuration of IMD. While this system may be used to recharge rechargeable power source 150, it may also be used to supply current to another type of load. For instance, such a system may be used to harvest energy from a secondary coil to power circuitry attached to the secondary coil. This may occur while current is also supplied to rechargeable power source 150, if desired.

The system of FIG. 7 is a hybrid of the circuits shown in FIGS. 4A and 5A. According to one aspect of the disclosure, this circuit maximizes the energy (e.g., RMS current) available to recharge rechargeable power source 150. Rechargeable power source 150 may be an electrical power source, such as a power source containing one or more capacitors and/or super capacitors. Alternatively or additionally, rechargeable power source 150 may be a chemical power source such as a lithium ion battery or any other type of chemical rechargeable battery.

The circuit of FIG. 7 maximizes energy available to rechargeable power source 150 by dynamically controlling the state of switch 152. When switch 152 is in a closed position so that node 154 is grounded, the circuit operates as a HWVD rectifier of the type shown in FIG. 5A. Conversely, when switch 152 is in an open position, this circuit operates as a full-wave rectifier.

Control logic 156 controls switch 152 so that, in one embodiment, this switch is always in a position that provides the best recharge efficiency. In one embodiment, this control may be based on a measure of the current and/or charge flowing to rechargeable power source 150, as measured by charge sensor 158. For instance, in one example, charge sensor 158 may be a Coulomb counter.

In one specific embodiment, during recharge, a primary coil 160 is coupled to a secondary coil 162 either inductively or via RF coupling. In those recharge situations wherein the coupling coefficient value is less than $k_x$, switch 152 is in the closed position to couple node 154 to ground. As a result, diodes 164 and 166 are not conducting current. Diodes 168 and 170, tuning capacitor 172 and rectification capacitor 174 operate as a HWVD rectifier that is similar to that of FIG. 5A. This circuit performs half-wave rectification in a manner that doubles the voltage level available to rechargeable power source 150.

When the coupling coefficient value reaches $k_x$, control logic 156 places switch 152 in the open state. As a result, node 154 will assume a negative voltage during one phase of the waveform that is induced across secondary coil 162. This allows current to flow through diodes 164 and 170 to rechargeable power source 150. At this time, diodes 166 and 168 will not be conducting current. When the voltage at node 154 is instead positive during the other phase of the waveform, current will flow through diodes 166 and 168 to rechargeable power source 150. During this phase, diodes 164 and 170 will not be conducting current. In this configuration, diodes 164, 166, 168, and 170 operate as a full-wave rectification circuit, increasing recharge efficiency for a coupling coefficient greater than $k_x$.

As discussed above, control is exerted over switch 152 by control logic 156. Control logic 156 may include one or more microprocessors, application-specific integrated circuits (ASICs), digital signal processors (DSPs), field-programmable gate arrays (FPGAs), discrete electronic components, control logic, and/or other circuitry. Data and/or programmed instructions needed to exercise this control may be stored within a storage device 157. For instance, programmed instructions that determine how switch 152 is to be configured may be stored within storage device 157 and executed by a microprocessor included within control logic 156.

As previously stated, in one embodiment, control exercised by control logic 156 may be based on the charge flowing to rechargeable power source 150, as measured by charge sensor 158. According to one method, control logic 156 may obtain some indication of the charge flowing to rechargeable power source 150 with the switch in a first state. Control logic 156 may then place the switch in a second state and obtain a second indication of the charge flowing to the power source 150. Control logic 156 may then select the state of switch 152 that results in the largest current to the rechargeable power source 150.

Other conditions may be monitored instead of, or in addition to, the current and/or charge flow for use in controlling the state of switch 152 in the manner discussed above. In another embodiment, voltage levels may be used as a measure of the strength of the signal induced on secondary coil 162. As an example, the voltage at node 173 may be measured by voltage sensor 175 for this purpose. This voltage may be measured by voltage sensor 175 after disconnecting the load (e.g., rechargeable power source 150) from the rest of the circuit, for example. Alternatively or additionally, voltages at other nodes in the circuit may be measured for this purpose. For instance, voltage across the secondary coil 162 may be used as an indication of the current being provided to the rechargeable power source 150 and/or to another load.

When monitoring voltage, control logic 156 may obtain an indication of the voltage at the selected circuit node with the switch in a first state. Control logic 156 may then place the switch in a second state and obtain a second indication of the voltage. Control logic 156 may then select the state of switch 152 that resulted in the largest voltage measurement, since this is also an indication of which configuration produces the largest current flow to the load.

Yet other conditions may be monitored to facilitate control of switch 152. For instance, the temperature of one or more of the components of the circuit of FIG. 7 may be measured with switch 152 in each of the two possible states. Temperature measurements may be obtained, for instance, at the secondary coil 162 or at the rechargeable power source 150 with the switch in both positions. Temperature measurements at other circuit nodes may likewise be obtained. Such temperature monitoring may be performed by one or more temperature sensors 177, which may be thermocouples or proportional-to-absolute-temperature (PTAT) sensors, for instance.

The measured temperatures may be compared to temperature profiles that provide a correlation between amplitude of current flow to the rechargeable power source 150 and the temperature at the monitored circuit node(s). These types of temperature profiles may be empirically derived, as by varying current received from the secondary coil and supplied to the power source 150 while measuring temperature at various nodes in the circuit. Temperature profiles may also be theoretically derived using circuit modeling techniques, simulation, and so on. Comparison of the temperature measurements to the profiles will indicate which switch position results in the largest current flow to the load. This switch position may then be selected.

Another embodiment of the system may be capable of monitoring more than one condition to determine the state of switch 152. The monitored conditions may be jointly taken into account, as by using a weighting formula, for instance. In this type of system, the one or more conditions that are monitored within the system to exercise control over switch 152 may be selectable by a user such as a clinician, if desired. Thus, many variations of the control mechanism implemented by control logic 156 may be contemplated by those skilled in the art.

In some system configurations, the ideal crossover point may shift based on device heating. Depending on device construction, coil orientation, and secondary coil proximity to metals, HWVD rectification may produce about twice the heat of FW rectification. For instance, this type of heating scenario may be likely if coupling between the primary and secondary coils is poor because of a secondary coil 162 that is angled within a body. Therefore, in one embodiment, temperature sensor 177 monitors the temperature of the system, and control logic 156 reverts to FW rectification if the temperature becomes too high. In this embodiment, this switch will occur even if HWVD rectification would provide a higher current flow to rechargeable power source 150.

In an alternative embodiment, the cross-over point in use within the system may shift during the course of a recharge session. For instance, if it is known that HWVD rectification will generate more heat than FW rectification, the cross-over point may be shifted to favor FW rectification over time as the recharge session progresses. This will aid in limiting the temperature during recharge below some predetermined limit. For instance, in reference to FIG. 6, the recharge session may be initiated with the cross-over point 146 at the location shown. However, as the recharge session progresses, the cross-over point may be lowered so that a switch to FW rectification will occur at a lower current amplitude than it would have occurred earlier in the recharge session. This type of shifting of the cross-over point may occur at predetermined time intervals as the recharge session progresses, in response to temperature monitoring, or in some other way. In a configuration wherein FW rectification produces more heat than HWVD rectification, the cross-over point may be shifted in the opposite direction, allowing HWVD rectification to be favored progressively more over the course of the recharge session.

It will be appreciated that many alternative embodiments are possible for the system of FIG. 7. For instance, whereas the system of FIG. 7 includes some circuit components in common between the half-wave and full-wave rectification circuits (e.g., diodes 168 and 170), this need not be the case. For instance, in another embodiment, separate dedicated components may be provided for each of the half-wave and full-wave rectification circuits. As another example, whereas the same secondary coil 162 is shown coupled to both the full-wave and half-wave rectification circuits, two dedicated secondary coils may be provided, with one being coupled to the half-wave rectification circuit and the other being coupled to the full-wave rectification circuit. In these alternative embodiments, the resulting circuit will consume more space and more power, however.

Figure 8A:
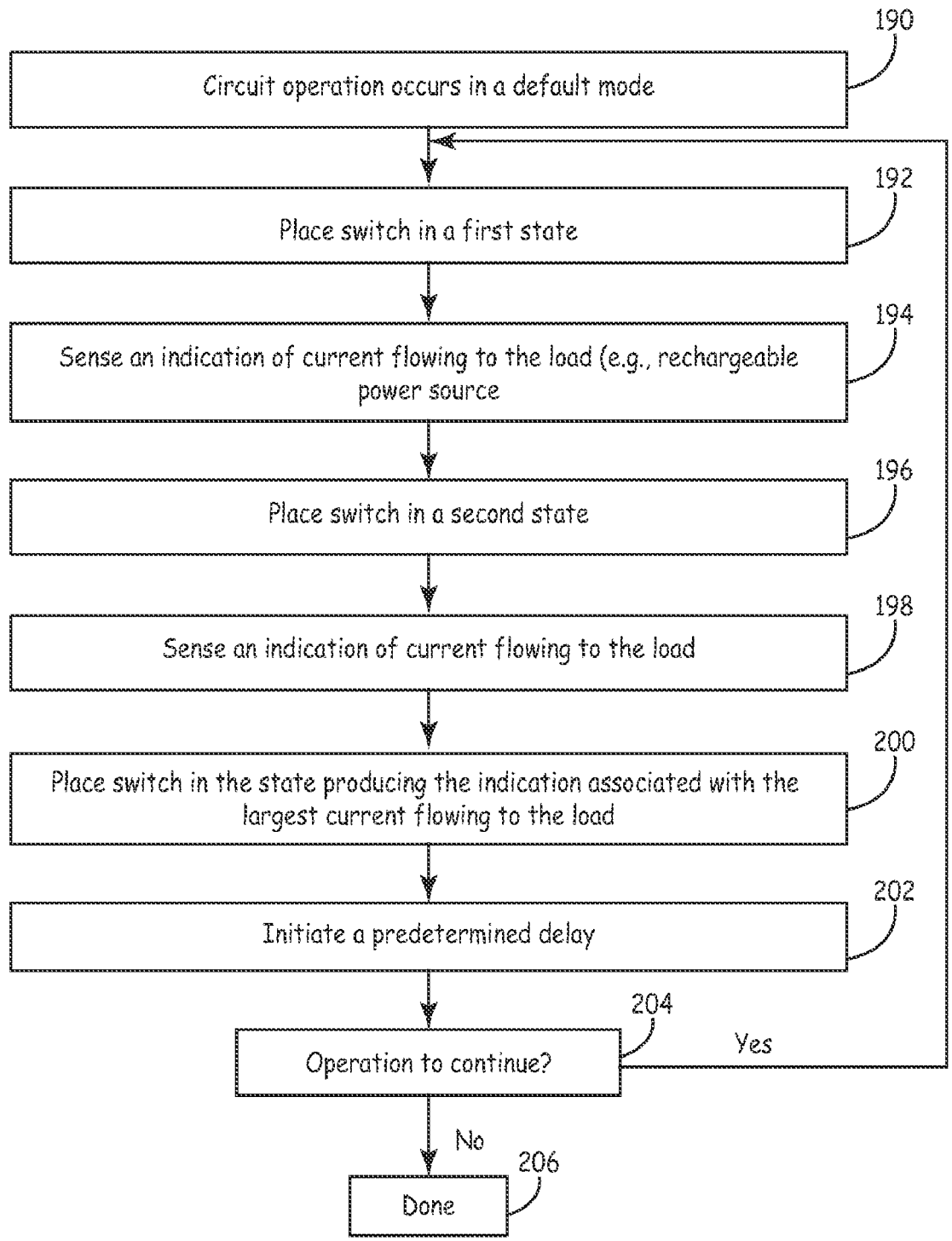
FIG. 8A is a flow diagram of one method according to the current disclosure.

FIG. 8A is a flow diagram illustrating one method according to the current disclosure. Upon circuit reset, the circuit is operated according to a default configuration, which may be associated with either full-wave rectification or HWVD configuration (190). In one embodiment, this default configuration may be programmably selected. Next, the switch is placed in a first state (192), which may be associated with a first one of the circuit configurations (either the full-wave rectification or the HWVD configuration). Some indication of the current flowing to the load may be sensed (194). This indication may be associated with charge and/or current, temperature, voltage, or any other indication that will provide an indication of the current flowing to the circuit load. The load will generally include a rechargeable power source, and may optionally include additional circuitry, such as circuitry that provides therapy to a patient. In one alternative embodiment, this load need not include a rechargeable power source.

Next, the switch may be placed in a second state, which is associated with the other configuration (196). The indication of the current flowing to the load is sensed again (198). Finally, the switch may be placed in whichever one of the first state or the second state resulted in the configuration producing the indication of highest current flow to the load (200).

A predetermined delay may then be initiated (202). In one embodiment, this delay may range from five seconds to two minutes. More specifically, this delay may range from fifteen seconds to forty-five seconds. In one particular embodiment, this delay will be approximately thirty seconds.

After the delay expires, if use of the rectification circuit may be discontinued (204), the process is completed (206). For instance, this decision may be made based on whether the rechargeable power source has been adequately recharged, as may be determined by the voltage across this power source or in some other manner. Otherwise, processing returns to step 192 and the steps of determining the optimal switch setting is repeated.

The foregoing discusses one mechanism of using closed-loop control to determine which rectification circuit is providing current to a load. Such closed-loop control involves sensing a condition such as current, voltage, and/or temperature within one or more nodes of the circuit and using the sensed conditions to determine a state of switch 152. In yet another embodiment of the disclosed techniques, control logic 156 controls the state of switch 152 by toggling between states at predetermined time intervals. These time intervals may be measured by a timer 156a included within control logic 156 or within other logic of the system. This timer may be implemented in software or hardware. Thus, this open-loop embodiment operates based on the state of timer 156a, with the switch being re-configured at timer expiration.

According to this aspect, switch 152 may be placed in each one of two states for roughly half of the time recharge is occurring based on the timer. Alternatively, switch 152 may be placed in a first state for a greater percentage of time than switch 152 is placed in the second state. For instance, full-wave rectification may be selected 60% of the time, with the HWVD rectifier being selected only 40% of the time. In one embodiment, the percentage of time switch 152 is placed in a given state may be programmably selected by a user such as a clinician.

Figure 8B:
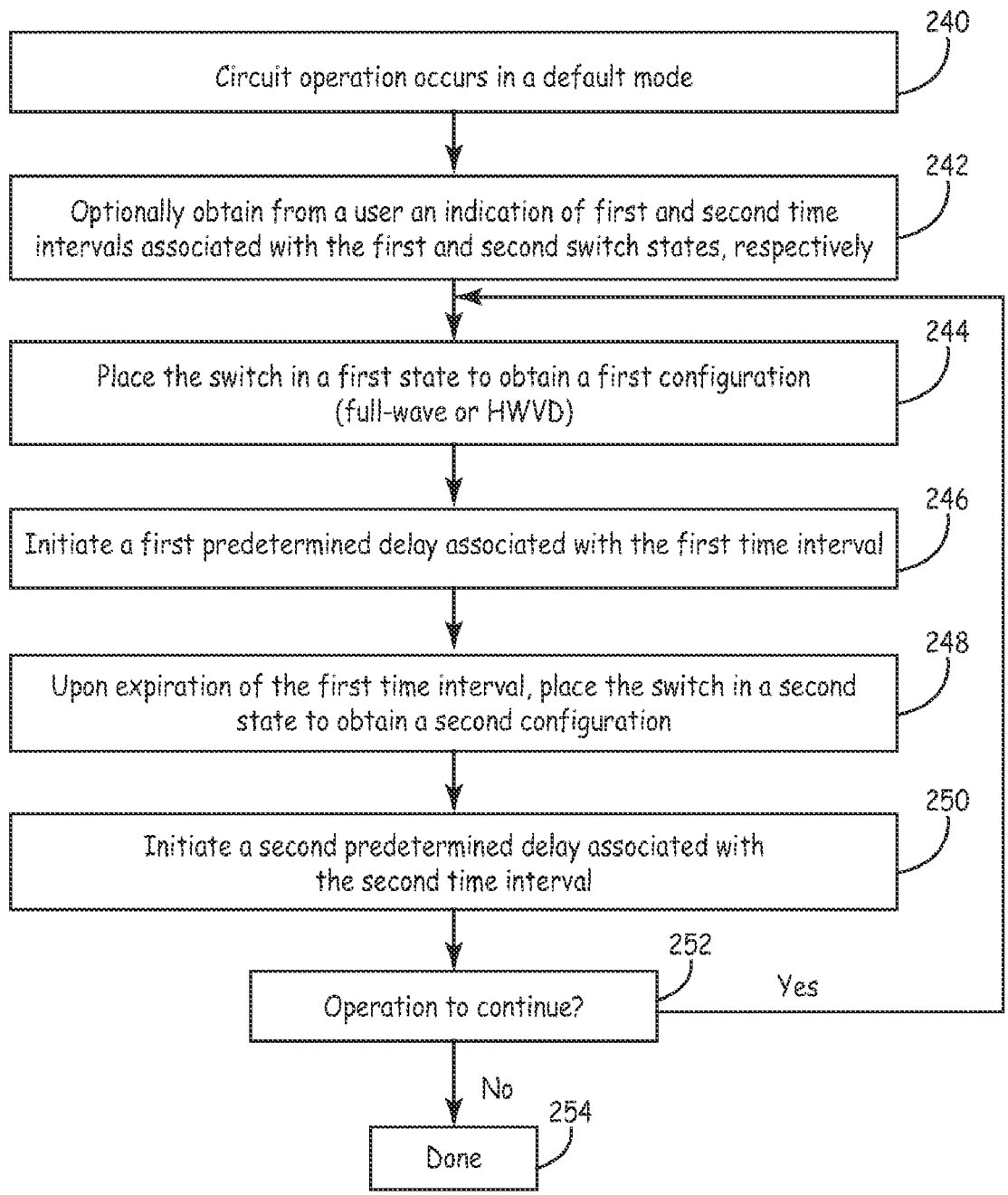
FIG. 8B is a flow diagram of another method according to the current disclosure.

FIG. 8B is a flow diagram illustrating an open-loop method according to one embodiment of the current disclosure. Upon reset of the system, circuit operation may commence operation in a default mode, which in one embodiment may be programmably selected (240). Information may optionally be obtained from a user to determine first and second time intervals that are associated with first and second switch states, respectively (242).

Next, the switch may be placed in a first state to obtain a first mode of circuit operation, which may be full-wave rectification or HWVD rectification (244). A first delay associated with the first time interval may be initiated (246). When this time elapses, as may be determined by monitoring a timer, the switch may be placed in a second state different from the first state to obtain the second mode of circuit operation (248). A second delay associated with the second time interval may be initiated (250).

After the second time interval expires, if use of the rectification circuit may be discontinued (252), the process is completed (254). For instance, this decision may be made based on whether the rechargeable power source has been adequately recharged, as may be determined by the voltage across this power source or in some other manner. Otherwise, processing returns to step 244 and the process is repeated.

The time periods used for the first and second intervals may be selected based on the application and on circuit configuration. In one embodiment, each of these time periods may range from five seconds to two minutes. In a more specific example, the time periods may range from fifteen seconds to forty-five seconds. In an even more specific embodiment, the time period of each interval may be thirty seconds. In other applications, longer or shorter intervals may be utilized. Moreover, the first time interval need not be equal to the second time interval if one type of configuration is to be employed more than the other configuration. Each of these time intervals may be programmably selected, if desired. For instance, a clinician may be allowed to select the interval lengths.

Another method of control involves using the values of monitored conditions that are known to exist at the cross-over point, such as cross-over point 146 of FIG. 6. As discussed above, for any given circuit configuration (e.g., configuration of the primary and secondary coils) a cross-over point may be determined for the circuit. This cross-over point determines a coupling coefficient at which the FWVD rectifier will provide approximately the same current as that provided by full-wave rectification.

A cross-over point for any given circuit configuration may be determined theoretically using calculations that take into account the coil configurations for the primary and secondary coils, as well as the other components of the circuit of FIG. 7. Alternatively, a cross-over point may be determined empirically, as by placing the circuit of FIG. 7 is a selected configuration (either HWVD or full-wave configuration) and then varying the orientation of the primary and secondary coils relative to each other to vary the coupling efficiency. Variations of coupling efficiency may be monitored using a power meter or a vector voltmeter. While the coupling efficiency is being varied, the current being provided to the load may be measured. Waveforms similar to those shown in FIG. 6 may thereby be plotted for each of the configurations. The point of intersection of the waveforms determines the cross-over point. This cross-over point will identify the cross-over current value, which is the current amplitude that will exist for the particular circuit configuration at the cross-over point. As previously mentioned, this cross-over point may be shifted during the course of the recharge session, if desired. This may be done so that the temperature of the system does not exceed a predetermined temperature limit, which may be a regulatory limit, a patient preference, a manufacturer's guideline, or some other type of limit.

Once the cross-over current value is determined, it may be used to configure switch 152. In particular, control logic 156 may utilize a measurement from charge sensor 158 to determine the current sensed at a particular moment in time. This current value may be compared to the cross-over current value. If the measured current value is less that the cross-over current value, switch 152 may be placed in the closed position for use as a HWVD rectifier. Periodically, the current may be measured again to determine whether coupling efficiency has changed. If the current increases to an amplitude exceeding the cross-over current, switch 152 may be opened to obtain a full-wave rectifier. Switch 152 may be retained in the open position so long as the current level does not decrease below the amplitude associated with the cross-over point. If the current amplitude does decrease below this level, the switch may again be closed.

If desired, some hysteresis may be incorporated into the control mechanism provided by control logic 156. For instance, the current may be required to increase some additional threshold amount above that associated with the cross-over point before control logic 156 will cause switch 152 to transition from a closed to an open state. Conversely, when the switch is in the open state, control logic 156 may require the current to transition below some threshold amount associated with the current at the cross-over point before the switch will be closed. This will prevent a scenario wherein the switch 152 is repeatedly being opened and closed because the current level is hovering around that associated with the cross-over point.

Other conditions may be monitored instead of, or in addition to, the current flow for use in controlling state of switch 152 in the manner discussed above. In another embodiment, the voltage at node 173 or the voltage across secondary coil 162 may be measured for this purpose. In particular, a measured voltage may be compared to a corresponding voltage associated with the cross-over point. This cross-over voltage may be determined empirically, using circuit theory calculations and/or by employing circuit modeling techniques in a manner similar to that described above. If the measured voltage is less than that associated with the cross-over voltage, HWVD rectification may be used. Otherwise, full-wave rectification may be employed.

Yet other conditions may be monitored to facilitate control of switch 152 in a similar manner. For instance, the temperature of one or more of the components of the circuit of FIG. 7 may be monitored and compared to corresponding temperature values associated with the cross-over point. For instance, the temperature of secondary coil 162 and/or rechargeable power source 150 may be used for this purpose. The values associated with the cross-over point may be empirically or theoretically determined. If the sensed temperature is above that known to exist at the cross-over point, control logic 156 may place switch 152 in an open position to obtain full-wave rectification. Otherwise, HWVD rectification will be selected by placing the switch in the closed position. In the manner discussed above, temperature sensor 177 may be used for this purpose.

A measurement of back-scattering may also be used to control the state of switch 152 in one embodiment. According to this aspect, control logic 156 may open, then close, a switch 153 one or more times. When switch 153 is closed, the terminals of secondary coil 162 are shorted to one another. While the switch is being opened and closed in this manner, a back-scatter detector within an external device such as back-scatter detector 83 within recharging device 70 (FIG. 2) will measure the back-scatter generated by this operation. The external device such as recharging device 70 may compare the sensed back-scatter value to a back-scatter value associated with the cross-over point. As was the case in the examples discussed above, this back-scatter value associated with the cross-over point may be empirically or theoretically determined. If the back-scatter value is larger than that associated with the cross-over point, the external device will determine recharging will optimally occur using full-wave rectification. Otherwise, HWVD rectification will be used. An indication of this determination may be provided to the IMD as via a telemetry communication. For instance, recharging device 70 may utilize telemetry module 85 and telemetry coil 87 to transmit this to IMD 2 via telemetry coil 89 and telemetry module 67. In response, control logic 156 will configure switch 152 in accordance with this determination. In this manner, the determination as to how the circuit of FIG. 7 is configured is made via an external device, rather than by the IMD.

Another embodiment of the system may be capable of monitoring more than one condition using cross-over values to determine the state of switch 152. The monitored conditions may be jointly taken into account, as by using a weighting formula, for instance. In this type of system, the one or more conditions that are used at any given moment in time to exercise control over switch 152 may be selectable by a user such as a clinician, if desired. Thus, many variations of the control mechanism implemented by control logic 156 may be contemplated by those skilled in the art.

Figure 8C:
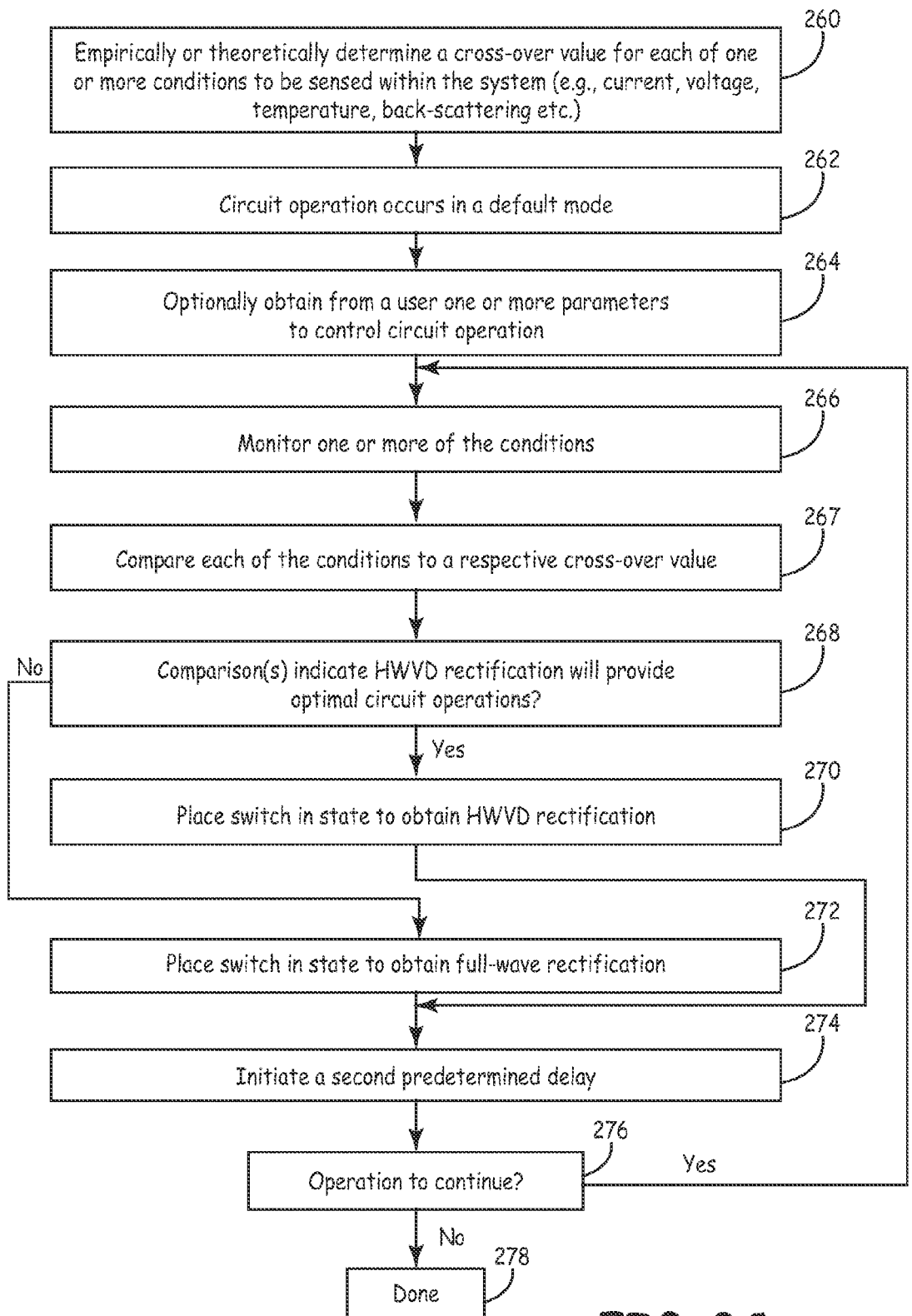
FIG. 8C is a flow diagram of yet another method according to the current disclosure.

FIG. 8C is a flow diagram illustrating another method according to the current disclosure. A cross-over value is determined for each of one or more conditions to be sensed within the recharge system (260). Such conditions may include an indication of charge or current flowing to the rechargeable power source, voltage at one or more nodes in the system, temperature at one or more nodes in the system, an amount of back-scatter, and so on. These values may be determined empirically, theoretically, using circuit modeling techniques, etc.

Upon reset of the system, circuit operation may commence in a default mode, which in one embodiment may be programmably selected (262). Information may optionally be obtained from a user to determine how circuit control will be performed (264). For instance, a clinician may indicate the conditions that are to be sensed to facilitate control.

Next, one or more of the conditions may be sensed within the circuit (266). Each of the sensed conditions may be compared to a respective cross-over value (267). For instance, a current flowing to the rechargeable power source may be compared to the current existing at the cross-over point in a manner described in reference to FIG. 6. This comparison step may optionally utilize hysteresis so that the value obtained from the monitored condition must increase or decrease some threshold amount above or below the cross-over value before the state of switch is changed.

Theses comparison(s) may then be used to determine the configuration in which to place the system. In particular, if the comparison(s) indicates operation using HWVD rectification will provide better recharge efficiency (268), the switch is placed in a state to obtain HWVD operation (270). For instance, in the circuit of FIG. 7, switch 152 is placed in the closed position. Otherwise, if optimal operation will not be obtained using HWVD rectification, the switch is placed in a state to obtain full-wave rectification (272). For instance, in FIG. 7, switch 152 is placed in the open position in this instance.

After the switch is positioned in the selected position according to either step 270 or 272, a predetermined delay may be initiated (274).

After the delay expires, if circuit operation is to be discontinued (e.g., because the rechargeable power source has been adequately recharged) (276), the process is completed (278). Otherwise, processing returns to step 266 and the steps of determining the optimal switch setting is repeated.

Those skilled in the art will appreciate that variations are possible within the scope of the invention. For instance, whereas the circuit is shown to be included in a neurostimulation device, it may alternatively be included in any other implantable medical device. Such a circuit may alternatively be included in external medical devices, or other devices that include rechargeable power sources. Various components and configurations are possible for use with the circuit of FIG. 7. For instance, one or more of the functions shown implemented in hardware may, in some instances, be implemented using programmed instructions or some combination of programmed instructions and hardware. Regarding the various described methods, the steps of the methods may be re-ordered in many instances and/or some steps may be eliminated entirely within the scope of the disclosure. Other steps may be added without changing the spirit of the disclosure. Thus, the description is to be considered illustrative only, with the scope of the invention to be determined by the Claims that follow.

What is claimed is:

1. A recharge system, comprising:
   a rechargeable power source;
   a half-wave voltage-doubling (HWVD) rectifier coupled to receive energy from a charging power source to recharge the rechargeable power source;
   a full-wave rectifier coupled to receive energy from the charging power source to recharge the rechargeable power source; and
   control logic configured to increase a rate at which the rechargeable power source is recharged by controlling which one of the HWVD rectifier and the full-wave rectifier is recharging the rechargeable power source at any given time.

2. The recharge system of claim 1, further comprising a switch
   configured
   to selectably couple the rechargeable power source to the HWVD rectifier or the full-wave rectifier, and wherein the control logic controls the state of the switch.

3. The recharge system of claim 2, wherein the control logic monitors a condition within the recharge system and controls the state of the switch based on the monitored condition.

4. The recharge system of claim 1, further comprising a sensor configured to provide an indication related to current flowing into the rechargeable power source, and wherein the control logic couples one of the HWVD rectifier and the full-wave rectifier to recharge the rechargeable power source based on the indication of current.

5. The recharge system of claim 4, wherein the indication of current indicates which one of the HWVD rectifier and the full-wave rectifier is capable of providing the largest current to the rechargeable power source at the time the coupling occurs.

6. The recharge system of claim 1, further comprising a sensor configured to provide an indication of a temperature within the recharge system, and wherein the control logic couples one of the HWVD rectifier and the full-wave rectifier to recharge the rechargeable power source based on the indication of temperature.

7. The recharge system of claim 6, wherein the indication of temperature is a temperature of a secondary coil.

8. The recharge system of claim 1, further comprising a sensor configured to provide an indication of a voltage within the recharge system, and wherein the control logic couples one of the HWVD rectifier and the full-wave rectifier to recharge the rechargeable power source based on the indication of voltage.

9. The recharge system of claim 1, further comprising:
   an implantable secondary recharge coil;
   a primary recharge coil configured to transfer energy to the secondary recharge coil; and
   a back-scatter detector configured to provide an indication of back-scatter between the primary recharge coil and the secondary recharge coil, and wherein the control logic couples one of the HWVD rectifier and the full-wave rectifier to supply the rechargeable power source with energy based on the indication of back-scatter.

10. The recharge system of claim 1, wherein while the rechargeable power source is being recharged by the recharge system, the control logic is configured to switch between coupling the rechargeable power source to receive energy from the HWVD rectifier and coupling the rechargeable power source to receive energy from the full-wave rectifier, and wherein the switching occurs at predetermined time intervals.

11. The recharge system of claim 1, further comprising one or more sensors configured to monitor one or more conditions within the recharge system, and wherein the control logic compares at least one of the monitored conditions to a respective cross-over value, and based on the comparison couples a selected one of the HWVD rectifier and the full-wave rectifier to recharge the rechargeable power source.

12. A system, comprising:
    a recharging device having a primary coil; and
    an implantable medical device comprising:
       a secondary coil configured to receive energy from the primary coil;
       a half-wave voltage-doubling (HWVD) rectifier coupled to the secondary coil;
       a full-wave rectifier coupled to the secondary coil;
       a rechargeable power source; and
       control logic configured to periodically select to which one of the HWVD rectifier and the full-wave rectifier the rechargeable power source is to be coupled to be recharged, thereby increasing efficiency of recharging the rechargeable power source.

13. The system of claim 12, wherein the HWVD rectifier comprises:
    a tuning capacitor coupled to the secondary coil; and
    two diodes coupled to the tuning capacitor;

and whereby the tuning capacitor and the two diodes are configured to perform recharge during a charging phase and a pumping phase.

14. The system of claim 12, further comprising a sensor configured to provide an indication of charge being supplied to the rechargeable power source by each of the HWVD rectifier and the full-wave rectifier, and wherein the control logic performs selection based on the indication of the charge being supplied.

15. The system of claim 12, wherein the control logic configures the rechargeable power source to be recharged by the HWVD rectifier during first time periods, and the control logic configures the rechargeable power source to be recharged by the full-wave rectifier during second time periods that alternate with the first time periods.

16. The system of claim 12, further comprising a sensor configured to provide an indication of temperature of the rechargeable power source and wherein the control logic performs selection based on the indication of the temperature.

17. The system of claim 12, wherein the recharging device includes a back-scatter detector configured to provide an indication of back-scatter received from the secondary coil, and wherein the control logic performs selection based on the indication of the back-scatter.

18. The system of claim 12, further including a sensor configured to provide an indication of voltage at one or more nodes within the system, and wherein the control logic performs selection based on the indication of voltage at the one or more nodes.

19. The system of claim 12, further comprising a sensor configured to sense a condition within the system, wherein the condition will reach a cross-over value when current provided by the HWVD rectifier to the rechargeable power source is substantially equal to current provided by the full-wave rectifier to the rechargeable power source for a same coupling coefficient value, and wherein the control logic performs selection based on a comparison between a sensed value of the condition and the cross-over value for the condition.

20. The recharge system of claim 1, further comprising the charging power source.

21. A method, comprising:
receiving energy, via a charging power source, to recharge a rechargeable power source of an implantable device; and
controlling, via control logic, which one of a HWVD rectifier and a full-wave rectifier is coupled to provide charge to the rechargeable power source at a given time to thereby increase a rate at which the received energy recharges the rechargeable power source.

22. The method of claim 21, further comprising monitoring a condition associated with recharging the rechargeable power source and wherein controlling which one of a HWVD rectifier and a full-wave rectifier is coupled to provide charge to the rechargeable power source comprises controlling which one of a HWVD rectifier and a full-wave rectifier is coupled to provide charge to the rechargeable power source based on the monitored condition.

23. The method of claim 22, wherein the monitored condition is an indication of current flowing into the rechargeable power source.

24. The method of claim 22, wherein the monitored condition is an indication of temperature associated with recharging the rechargeable power source.

25. The method of claim 22, wherein temperature is the temperature of the secondary coil.

26. The method of claim 22, wherein the monitored condition is an indication of voltage associated with recharging the rechargeable power source.

27. The method of claim 22, wherein the monitored condition is an indication of back-scatter.

28. The method of claim 21, wherein controlling which one of a HWVD rectifier and a full-wave rectifier is coupled to provide charge to the rechargeable power source comprises controlling, at predetermined time intervals, which one of the HWVD rectifier and the full-wave rectifier is coupled to provide charge to the rechargeable power source.

29. The method of claim 21, further comprising:
monitoring one or more conditions associated with recharging the rechargeable power source;
comparing at least one of the monitored conditions to a respective cross-over value; and
wherein controlling which one of a HWVD rectifier and a full-wave rectifier is coupled to provide charge to the rechargeable power source comprises controlling which one of a HWVD rectifier and a full-wave rectifier is coupled to provide charge to the rechargeable power source based on the comparison.

30. The method of claim 21, wherein controlling which one of a HWVD rectifier and a full-wave rectifier is coupled to provide charge to the rechargeable power source further comprises:
coupling the rechargeable power source to receive charge from the full-wave rectifier;
initiating a first time delay; and
upon expiration of the first time delay, coupling the rechargeable power source to receive charge from the HWVD rectifier.

* * * * *